United States Patent [19]

Tsushima et al.

[11] Patent Number: 4,664,698
[45] Date of Patent: May 12, 1987

[54] ETHER COMPOUND, AND AN INSECTICIDAL AND ACARICIDAL COMPOSITION CONTAINING IT AS AN ACTIVE INGREDIENT

[75] Inventors: Kazunori Tsushima, Nishinomiya; Noritada Matsuo, Itami; Hirosi Kisida, Tokyo; Toshihiko Yano, Ikoma, all of Japan

[73] Assignee: Sumitomo Chemical Company, Limited, Osaka, Japan

[21] Appl. No.: 773,615

[22] Filed: Sep. 9, 1985

[30] Foreign Application Priority Data

Sep. 21, 1984 [JP] Japan .................................. 59-199131
Jun. 21, 1985 [JP] Japan .................................. 60-136269

[51] Int. Cl.$^4$ .................... A01N 43/40; C07D 213/61; C07D 213/62; C07C 43/02
[52] U.S. Cl. .......................................... 71/94; 71/121; 71/124; 546/301; 546/302; 568/637; 564/431
[58] Field of Search ................. 546/301, 302; 568/637; 564/431; 71/94, 121, 124

[56] References Cited

U.S. PATENT DOCUMENTS 4,214,086  7/1980  Fah ........................................ 568/637

FOREIGN PATENT DOCUMENTS 0013144  6/1980  European Pat. Off. ............. 564/431
2502786  7/1976  Fed. Rep. of Germany ...... 568/637
015777   4/1976  United Kingdom ................ 568/637

OTHER PUBLICATIONS

Chemical Abstracts, John et al., vol. 88, No. 3; 22354n, 1977, pp. 15,16,31,28.
March, J. Adv. Org. Chem., pp. 406–407.
Morrison et al., Organic Chemistry 3rd Ed., pp. 187–188.

Primary Examiner—Henry R. Jiles
Assistant Examiner—J. Richter
Attorney, Agent, or Firm—Stevens, Davis, Miller & Mosher

[57] ABSTRACT

An ether compound represented by the following general formula (I), its production method and an insecticidal and acaricidal composition containing as an active ingredient:

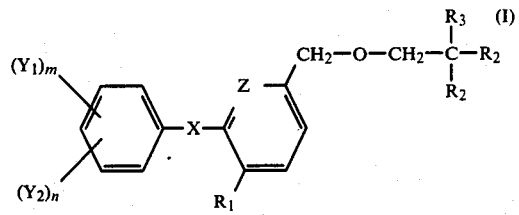

wherein X represents an oxygen atom or a group represented by the formula —NH—; when X represents an oxygen atom, Z represents a nitrogen atom or a group represented by the formula —CH═; when X represents —NH—, Z represents —CH═; when X represents an oxygen atom and Z represents a nitrogen atom, or when X represents —NH—, $R_1$ represents a hydrogen or fluorine atom; when X represents an oxygen atom and Z represents —CH═, $R_1$ represents a fluorine atom; $Y_1$ and $Y_2$, which may be identical or different, represent a hydrogen or halogen atom or an alkyl, haloalkyl, alkoxyl or haloalkoxyl group; m and n represent an integer of 1 to 4 and the sum of them is not more than 5; $R_2$ represents a methyl group or a chlorine atom; and $R_3$ represents a methyl group, a halogen atom or a methoxy group.

16 Claims, No Drawings

ETHER COMPOUND, AND AN INSECTICIDAL AND ACARICIDAL COMPOSITION CONTAINING IT AS AN ACTIVE INGREDIENT

The present invention relates to a novel ether compound represented by the general formula (I) described below, its production method and an insecticidal and acaricidal composition containing it as an active ingredient:

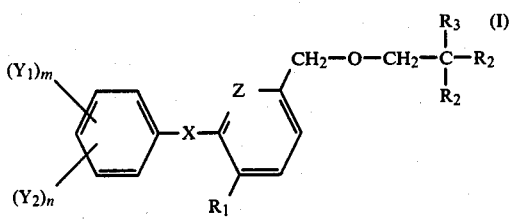

wherein X represents an oxygen atom or a group represented by the formula —NH—; when X represents an oxygen atom, Z represents a nitrogen atom or a group represented by the formula —CH=; when X represents —NH—, Z represents —CH=; when X represents an oxygen atom and Z represents a nitrogen atom, or when X represents —NH—, $R_1$ represents a hydrogen or fluorine atom; when X represents an oxygen atom and Z represents —CH=, $R_1$ represents a fluorine atom; $Y_1$ and $Y_2$, which may be identical or different, represent a hydrogen or halogen (e.g. fluorine, chlorine, bromine) atom or an alkyl (e.g. $C_{1-5}$ lower alkyl), haloalkyl (e.g. $C_{1-5}$ lower alkyl substituted with fluorine, chlorine or bromine atom), alkoxyl (e.g. $C_{1-5}$ lower alkoxyl) or haloalkoxyl (e.g. $C_{1-5}$ lower alkoxyl substituted with fluorine, chlorine or bromine atom) group; m and n represent an integer of 1 to 4 and the sum of them is not more than 5; $R_2$ represents a methyl group or a chlorine atom; and $R_3$ represents a methyl group, a halogen (e.g. chlorine, bromine) atom or a methoxy group.

The present inventors extensively studied for the purpose of developing compounds having excellent insecticidal activity, and as a result, found that the present compound represented by the foregoing general formula (I) has characteristics that (1) it has a high insecticidal effect and (2) its insecticidal effect on insect pests resistant to organic phosphates or carbamates is also excellent. The present inventors thus attained to the present invention.

As examples of insect pests to which the present compound is particularly effective, there are given for example Hemiptera such as planthoppers, leafhoppers, aphides, bugs, etc., Lepidoptera such as rice stem borer (Chilo suppressalis), armyworms and cutworms, etc., Diptera such as common mosquito (Culex pipiens pallens), housefly (Musca domestica), etc., Diclyoptera such as German cockroach (Blattella germanica), etc., Coleoptera, Orthoptera, mites such as carmine spider mite (Tetranychus cinnabarinus), citrus red mite (Panonychus citri), etc.

In the present compound represented by the foregoing general formula (I), the compound wherein one of $Y_1$ and $Y_2$ represents hydrogen atom and the other represents a hydrogen or halogen atom or an alkyl group; the sum of m and n is 2; and $R_3$ represents a methyl group or a halogen atom is preferable and the compound wherein X represent a group represented by the formula —NH—, or X represents an oxygen atom and Z represents a nigrogen atom; one of $Y_1$ and $Y_2$ represents a hydrogen atom and the other represents a hydrogen, chlorine or bromine atom or a methyl group; the sum of m and n is 2; and both $R_2$ and $R_3$ are identical each other and represent a methyl group or a chlorine atom is more preferable.

The present compound can be produced, for example, by the following methods.

Method A

A method for producing the ether compound represented by the general formula,

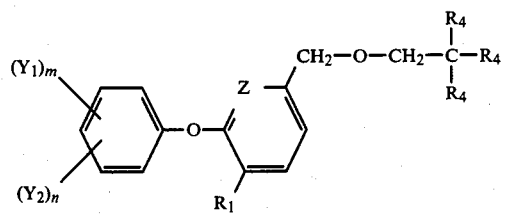

wherein Z, $R_1$, $Y_1$, $Y_2$, m and n have the same meanings as described above, and $R_4$ represents a methyl group or chlorine atom, by reacting a compound represented by the general formula (III),

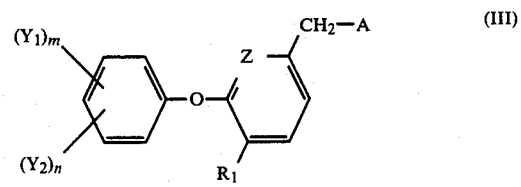

wherein Z, $R_1$, $Y_1$, $Y_2$, m and n have the same meanings as described above, and A represents a halogen atom, with an alcohol compound represented by the general formula (IV),

wherein $R_4$ has the same meaning as described above, in the presence of a base.

More particularly, the above ether compound can be produced by reacting the alcohol compound represented by the foregoing general formula (IV) with a base (e.g. alkali metal hydride, alkali metal alkoxide, alkyl lithium, alkali metal carbonate, alkali metal hydroxide) in an inert organic solvent to produce the alkali metal salt thereof and then reacting the salt with the compound represented by the general formula (III) at a temperature over 0° C. for 1 to 72 hours. As examples of the inert organic solvent, there are given for example aprotic polar solvents (e.g. dimethylformamide, dimethyl sulfoxide), ethers (e.g. tetrahydrofuran, 1,4-dioxane, ethylene glycol dimethyl ether) and aromatic hydrocarbons (e.g. benzene, toluene).

Method B

A method for producing the ether compound represented by the general formula,

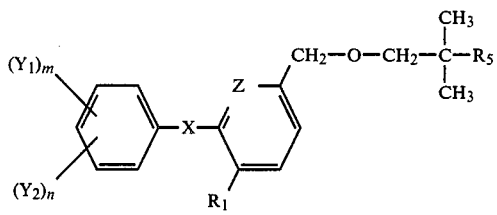

wherein X, Z, R$_1$, Y$_1$, Y$_2$, m and n have the same meanings as described above, and R$_5$ represents a chlorine or bromine atom or a methoxy group, by reacting a compound represented by the general formula (V),

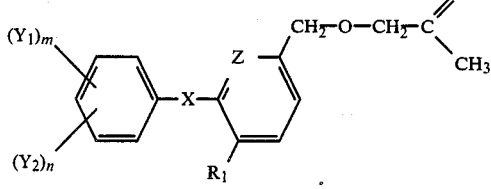

(V)

wherein X, Z, R$_1$, Y$_1$, Y$_2$, m and n have the same meanings as described above, with a compound represented by the general formula (VI),

HR$_5$ (VI)

wherein R$_5$ has the same meaning as described above.

More particularly, the above ether compound wherein a substituent R$_5$ is a chlorine or bromine atom can be produced by reacting the compound represented by the foregoing general formula (V) with a compound represented by the general formula (VII),

HR$_7$ (VII)

wherein R$_7$ represents a chlorine or bromine atom, in an inert organic solvent for 1 to 12 hours at a temperature from $-50°$ C. to room temperature. As examples of the inert organic solvent, there are given for example alcohols (e.g. methanol, ethanol), halogenated hydrocarbons (e.g. carbon tetrachloride, chloroform) and lower aliphatic carboxylic acids (e.g acetic acid, propionic acid).

Also, the above ether compound wherein a substituent R$_5$ is a methoxy group can be produced by reacting the compound represented by the general formula (V) with methanol at a temperature from $-10°$ C. to room temperature for 1 to 12 hours in the presence of mercuric acetate and then with an alkali hydroxide at a temperature from $0°$ C. to room temperature for 1 to 24 hours, and then reacting the resulting product with alkali borohydride at a temperature from $0°$ C. to room temperature.

In the method B, the compound represented by the general formula (V) can be produced, for example, through the following routes:

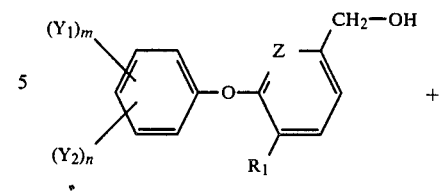
1

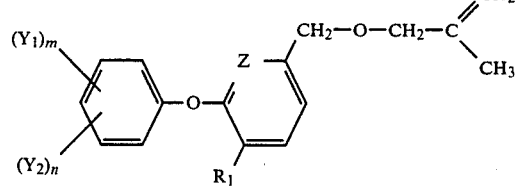

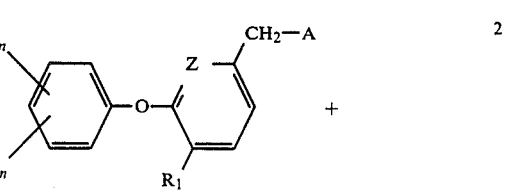

2

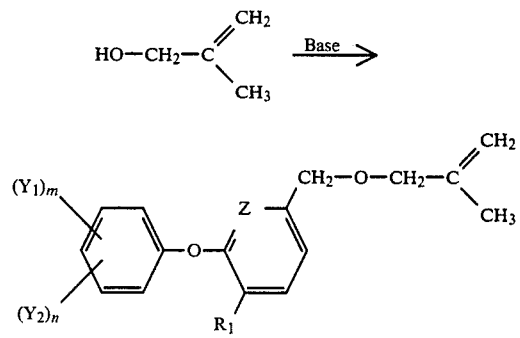

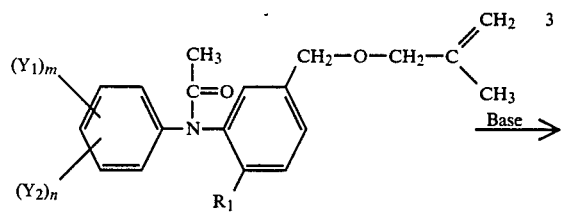

3

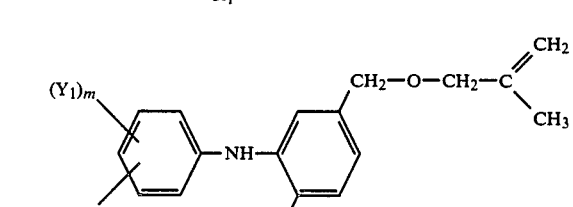

wherein Z, R$_1$, Y$_1$, Y$_2$, m, n and A have the same meanings as described above.

Method C

A method for producing the ether compound represented by the general formula,

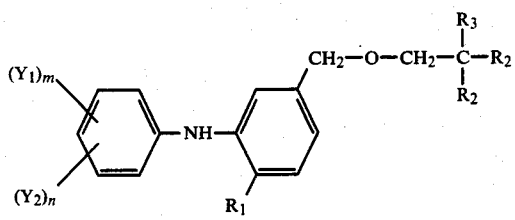
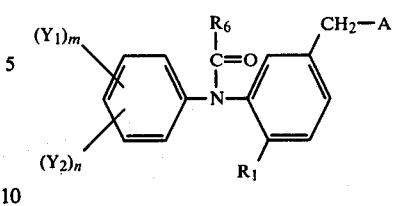

wherein $R_1$, $Y_1$, $Y_2$, m, n, $R_2$ and $R_3$ have the same meanings as described above, by deacylating a compound represented by the general formula (VIII),

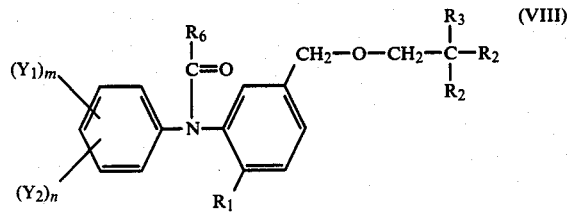

(VIII)

wherein $R_1$, $Y_1$, $Y_2$, m, n, $R_2$ and $R_3$ have the same meanings as described above, and $R_6$ represents a lower alkyl group.

More particularly, the above ether compound can be produced by reacting the compound represented by the foregoing general formula (VIII) with a base (e.g. sodium hydroxide, potassium hydroxide, calcium hydroxide, sodium alkoxide, potassium carbonate) in an inert organic solvent for 1 to 72 hours at a temperature from room temperature to the boiling point of the solvent. As examples of the inert organic solvent, there are given for example alcohol solvents (e.g. methanol, ethanol), ether solvents (e.g. tetrahydrofuran, 1,2-dimethoxyethane, 1,4-dioxane), water and mixed solvents of water with the alcohol or ether solvent. Also, the above ether compound can be produced by reacting the compound represented by the general formula (VIII) with an acid (e.g. hydrochloric acid, sulfuric acid) in the presence or not of the inert organic solvent at a temperature from room temperature to 100° C. for 1 to 48 hours. In the method C, the compound represented by the general formula (VIII) can be produced, for example, through the following routes:

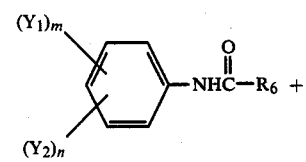

1

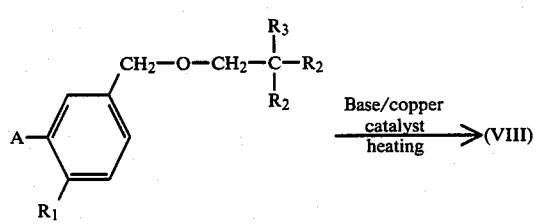

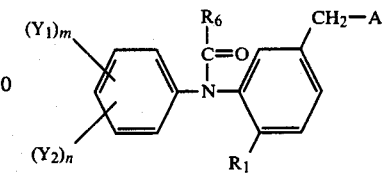

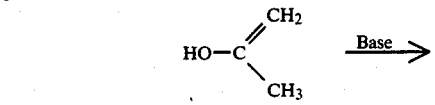

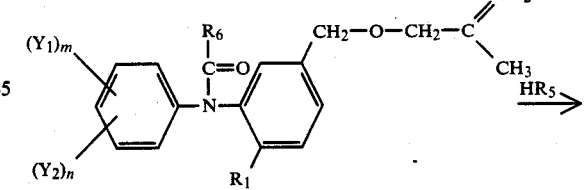

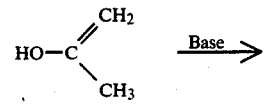

3

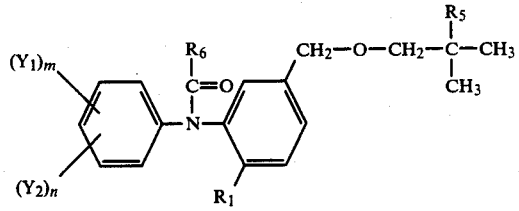

wherein $R_1$, $Y_1$, $Y_2$, m, n, $R_2$, $R_4$, $R_5$, $R_6$ and A have the same meanings as described above.

Method D

A method for producing the ether compound represented by the general formula,

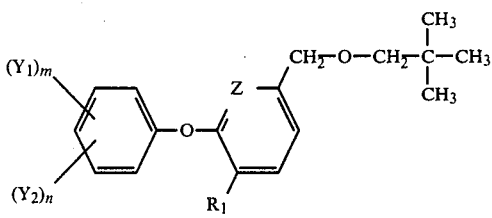

wherein Z, $R_1$, $Y_1$, $Y_2$, m and n have the same meanings as described above, by reacting a compound represented by the general formula (IX),

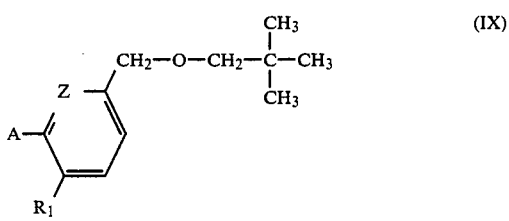

wherein Z, $R_1$ and A have the same meanings as described above, with a phenol derivative represented by the general formula (X),

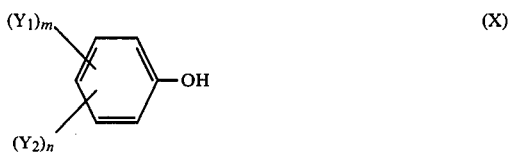

wherein $Y_1$, $Y_2$, m and n have the same meanings as described above, in the presence of a base.

More particularly, the above ether compound can be produced by reacting the compound represented by the general formula (X) with the compound represented by the general formula (IX) at 100° to 200° C. for 1 to 48 hours with or without an inert solvent in the presence of a base (e.g. sodium hydride, potassium hydride, potassium tertbutoxide, potassium carbonate, sodium hydroxide, potassium hydroxide) and in the presence or absence of a copper catalyst (e.g. cuprous chloride, cuprous bromide, cuprous iodide, copper powder, copper acetate, cupric chloride). This reaction is preferably carried out in an inert gas atmosphere (e.g. nitrogen gas). As examples of the inert solvent, there are given for example aprotic polar solvents such as dimethylformamide, dimethylacetamide, dimethyl sulfoxide, hexamethylphosphoroamide, 1,3-dimethylimidazolidinone, etc,. In the method D, the compound represented by the general formula (IX) can be produced, for example, through the following route:

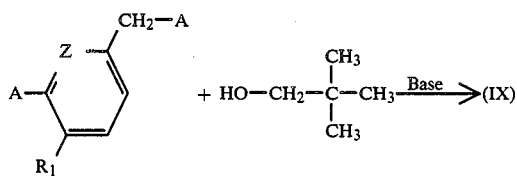

wherein Z, $R_1$ and A have the same meanings as described above.

Examples of the ether compound which can be produced by the above methods A to D will be given below:

6-Phenoxy-2-pyridylmethyl neopentyl ether
6-(4-Chlorophenoxy)-2-pyridylmethyl neopentyl ether
6-(4-Bromophenoxy)-2-pyridylmethyl neopentyl ether
6-(4-Fluorophenoxy)-2-pyridylmethyl neopentyl ether
6-(4-Methylphenoxy)-2-pyridylmethyl neopentyl ether
6-(4-Ethylphenoxy)-2-pyridylmethyl neopentyl ether
6-(4-Propylphenoxyl)-2-pyridylmethyl neopentyl ether
6-(4-tert-Butylphenoxy)-2-pyridylmethyl neopentyl ether
6-(4-Butylphenoxy)-2-pyridylmethyl neopentyl ether
6-(4-Methoxyphenoxy)-2-pyridylmethyl neopentyl ether
6-(4-Ethoxyphenoxy)-2-pyridylmethyl neopentyl ether
6-(4-Propyloxyphenoxy)-2-pyridylmethyl neopentyl ether
6-(4-Methyl-2-bromophenoxy)-2-pyridylmethyl neopentyl ether
6-(4-Methyl-2-chlorophenoxy)-2-pyridylmethyl neopentyl ether
6-(2,4-Dichlorophenoxy)-2-pyridylmethyl neopentyl ether
6-(4-Chloro-2-fluorophenoxy)-2-pyridylmethyl neopentyl ether
6-(4-Bromo-2-fluorophenoxy)-2-pyridylmethyl neopentyl ether
6-(4-Bromo-2-methylphenoxy)-2-pyridylmethyl neopentyl ether
6-(2,6-Dichlorophenoxy)-2-pyridylmethyl neopentyl ether
6-(2,6-Difluorophenoxy)-2-pyridylmethyl neopentyl ether
6-(2,4-Difluorophenoxy)-2-pyridylmethyl neopentyl ether
6-Phenoxy-5-fluoro-2-pyridylmethyl neopentyl ether
6-(4-(Chlorophenoxy)-5-fluoro-2-pyridylmethyl neopentyl ether
6-(4-Bromophenoxy)-5-fluoro-2-pyridylmethyl neopentyl ether
6-(4-Fluorophenoxy)-5-fluoro-2-pyridylmethyl neopentyl ether
6-(4-Methylphenoxy)-5-fluoro-2-pyridylmethyl neopentyl ether
6-(4-Ethylphenoxy)-5-fluoro-2-pyridylmethyl neopentyl ether
6-(4-Propylphenoxy)-5-fluoro-2-pyridylmethyl neopentyl ether
6-(4-tert-Butylphenoxy)-5-fluoro-2-pyridylmethyl neopentyl ether
6-(4-n-Butylphenoxy)-5-fluoro-2-pyridylmethyl neopentyl ether
6-(4-Methoxyphenoxy)-5-fluoro-2-pyridylmethyl neopentyl ether
6-(4-Ethoxyphenoxy)-5-fluoro-2-pyridylmethyl neopentyl ether
6-(4-Propyloxyphenoxy)-5-fluoro-2-pyridylmethyl neopentyl ether
6-(4-Methoxy-2-bromophenoxy)-5-fluoro-2-pyridylmethyl neopentyl ether
6-(4-Methyl-2-chlorophenoxy)-5-fluoro-2-pyridylmethyl neopentyl ether
6-(2,4-Dichlorophenoxy)-5-fluoro-2-pyridylmethyl neopentyl ether
6-(4-Chloro-2-fluorophenoxy)-5-fluoro-2-pyridylmethyl neopentyl ether 6-(4-Bromo-2-fluorophenoxy)-5-fluoro-2-pyridylmethyl neopentyl ether
6-(4-Bromo-2-methylphenoxy)-5-fluoro-2-pyridylmethyl neopentyl ether
6-(2,6-Dichlorophenoxy)-5-fluoro-2-pyridylmethyl neopentyl ether
6-(2,6-Difluorophenoxy)-5-fluoro-2-pyridylmethyl neopentyl ether
6-(2,4-Difluorophenoxy)-5-fluoro-2-pyridylmethyl neopentyl ether
6-Phenoxy-2-pyridylmethyl 2,2,2-trichloroethyl ether
6-(4-Chlorophenoxy)-2-pyridylmethyl 2,2,2-trichloroethyl ether
6-(4-Bromophenoxy)-2-pyridylmethyl 2,2,2-trichloroethyl ether
b 6-(4-Fluorophenoxy)-2-pyridylmethyl 2,2,2-trichloroethyl ether
6-(4-Methylphenoxy)-2-pyridylmethyl 2,2,2-trichloroethyl ether
6-(4-Ethylphenoxy)-2-pyridylmethyl 2,2,2-trichloroethyl ether
6-(4-Methoxyphenoxy)-2-pyridylmethyl 2,2,2-trichloroethyl ether
6-(4-Chloro-2-fluorophenoxy)-2-pyridylmethyl 2,2,2-trichloroethyl ether
6-(2,6-Dichlorophenoxy)-2-pyridylmethyl 2,2,2-trichloroethyl ether
6-(2,6-Difluorophenoxy)-2-pyridylmethyl 2,2,2-trichloroethyl ether
6-(2,4-Difluorophenoxy)-2-pyridylmethyl 2,2,2-trichloroethyl ether
6-Phenoxy-5-fluoro-2-pyridylmethyl 2-chloro-2-methylpropyl ether
6-(4-Chlorophenoxy)-5-fluoro-2-pyridylmethyl 2-bromo-2-methylpropyl ether
6-(4-Bromophenoxy)-5-fluoro-2-pyridylmethyl 2-chloro-2-methylpropyl ether
6-(4-Fluorophenoxy)-5-fluoro-2-pyridylmethyl 2-methyl-2-methoxypropyl ether
6-(4-Methylphenoxy)-2-pyridylmethyl 2-chloro-2-methylpropyl ether
6-(4-Methoxyphenoxy)-5-fluoro-2-pyridylmethyl 2-chloro-2-methylpropyl ether
6-(4-Chloro-2-fluorophenoxy)-2-pyridylmethyl 2-bromo-2-methylpropyl ether
6-(4-Bromo-2-fluorophenoxy)-2-pyridylmethyl 2-chloro-2-methylpropyl ether
6-(2,6-Difluorophenoxy)-5-fluoro-2-pyridylmethyl 2-chloro-2-methylpropyl ether
6-(2,4-Difluorophenoxy)-2-pyridylmethyl 2-bromo-2-methylpropyl ether
6-Phenoxy-5-fluoro-2-pyridylmethyl 2,2,2-trichloroethyl ether
6-(4-Chlorophenoxy)-5-fluoro-2-pyridylmethyl 2,2,2-trichloroethyl ether
6-(4-Bromophenoxy)-5-fluoro-2-pyridylmethyl 2-methoxy-2-methylpropyl ether
6-(4-Fluorophenoxy)-5-fluoro-2-pyridylmethyl 2-methoxy-2-methylpropyl ether
6-(4-Methylphenoxy)-5-fluoro-2-pyridylmethyl 2,2,2-trichloroethyl ether
6-(4-Methoxyphenoxy)-5-fluoro-2-pyridylmethyl 2,2,2-trichloroethyl ether
6-(4-Bromo-2-fluorophenoxy)-5-fluoro-2-pyridylmethyl 2,2,2-trichloroethyl ether
6-(4-Bromo-2-methylphenoxy)-5-fluoro-2-pyridylmethyl 2,2,2-trichloroethyl ether
6-(2,6-Dichlorophenoxy)-5-fluoro-2-pyridylmethyl 2,2,2-trichloroethyl ether
6-(2,6-Difluorophenoxy)-5-fluoro-2-pyridylmethyl 2,2,2-trichloroethyl ether
6-(2,4-Difluorophenoxy)-5-fluoro-2-pyridylmethyl 2,2,2-trichloroethyl ether
6-(4-Chloro-2-fluorophenoxy)-5-fluoro-2-pyridylmethyl 2,2,2-trichloroethyl ether
3-Anilino-4-fluorobenzyl neopentyl ether
3-(4-Chloroanilino)-4-fluorobenzyl neopentyl ether
3-(4-Fluoroanilino)-4-fluorobenzyl neopentyl ether
3-(4-Bromoanilino)-4-fluorobenzyl neopentyl ether
3-(4-Methylanilino)-4-fluorobenzyl neopentyl ether
3-(4-Ethylanilino)-4-fluorobenzyl neopentyl ether
3-(4-n-Propylanilino)-4-fluorobenzyl neopentyl ether
3-(4-iso-Propylanilino)-4-fluorobenzyl neopentyl ether
3-(4-n-Butylanilino)-4-fluorobenzyl neopentyl ether
3-(4-Methoxyanilino)-4-fluorobenzyl neopentyl ether
3-(4-Ethoxyanilino)-4-fluorobenzyl neopentyl ether
3-(4-Difluoromethoxyanilino)-4-fluorobenzyl neopentyl ether
3-(4-Pentafluoroethoxyanilino)-4-fluorobenzyl neopentyl ether
3-(4-Chloro-2-fluoroanilino)-4-fluorobenzyl neopentyl ether
3-(4-Chloro-2-methylanilino)-4-fluorobenzyl neopentyl ether
3-(4-Bromo-2-fluoroanilino)-4-fluorobenzyl neopentyl ether
3-(4-Bromo-2-methylanilino)-4-fluorobenzyl neopentyl ether
3-(2,4-Dimethylanilino)-4-fluorobenzyl neopentyl ether
3-(2,4-Dichloroanilino)-4-fluorobenzyl neopentyl ether
3-(2,4-Difluoroanilino)-4-fluorobenzyl neopentyl ether
3-(2,6-Difluoroanilino)-4-fluorobenzyl neopentyl ether
3-(2,6-Dichloroanilino)-4-fluorobenzyl neopentyl ether
3-(2-Chloro-6-fluoroanilino)-4fluorobenzyl neopentyl ether
3-Anilino-4-fluorobenzyl 2,2,2-trichloroethyl ether
3-(4-Chloroanilino)-4-fluorobenzyl 2,2,2-trichloroethyl ether
3-(4-Fluoroanilino)-4-fluorobenzyl 2,2,2-trichloroethyl ether
3-(4-Bromoanilino)-4-fluorobenzyl 2,2,2-trichloroethyl ether
3-(4-Methylanilino)-4-fluorobenzyl 2,2,2-trichloroethyl ether
3-(4-Ethylanilino)-4-fluorobenzyl 2,2,2-trichloroethyl ether
3-(4-Methoxyanilino)-4-fluorobenzyl 2,2,2-trichloroethyl ether
3-(4-Chloro-2-fluoroanilino)-4-fluorobenzyl 2,2,2-trichloroethyl ether
3-(4-Chloro-2-methylanilino)-4-fluorobenzyl 2,2,2-trichloroethyl ether
3-(4-Bromo-2-fluoroanilino)-4-fluorobenzyl 2,2,2-trichloroethyl ether
3-(2,4-Difluoroanilino)-4-fluorobenzyl 2,2,2-trichloroethyl ether
3-(2,6-Difluoroanilino)-4-fluorobenzyl 2,2,2-trichloroethyl ether
3-(2,6-Dichloroanilino)-4-fluorobenzyl 2,2,2-trichloroethyl ether
3-(2-Chloro-6-fluoroanilino)-4-fluorobenzyl 2,2,2-trichloroethyl ether
3-Anilino-4-fluorobenzyl 2-chloro-2-methylpropyl ether 3-(4-Chloroanilino)-4-fluorobenzyl 2-bromo-2-methylpropyl ether
3-(4-Fluoroanilino)-4-fluorobenzyl 2-methoxy-2-methylpropyl ether
3-(4-Bromoanilino)-4-fluorobenzyl 2-chloro-2-methylpropyl ether
3-(4-Methylanilino)-4-fluorobenzyl 2-methoxy-2-methylpropyl ether
3-(4-Methoxyanilino)-4-fluorobenzyl 2-chloro-2-methylpropyl ether
3-(4-Difluoromethoxyanilino)-4-fluorobenzyl 2-chloro-2-methylpropyl ether
3-(4-Chloro-2-fluoroanilino)-4-fluorobenzyl 2-methoxy-2-methylpropyl ether
3-(2,4-Difluoroanilino)-4-fluorobenzyl 2-chloro-2-methylpropyl ether
3-(2,6-Difluoroanilino)-4-fluorobenzyl 2-chloro-2-methylpropyl ether
3-(2,6-Dichloroanilino)-4-fluorobenzyl 2-methoxy-2-methylpropyl ether
3-(2-Chloro-6-fluoroanilino)-4-fluorobenzyl 2-methoxy-2-methylpropyl ether
3-(4-Trifluoromethoxyanilino)-4-fluorobenzyl neopentyl ether
3-(4-Trifluoromethoxyanilino)-4-fluorobenzyl 2,2,2-trichloroethyl ether
3-Anilinobenzyl neopentyl ether
3-Anilinobenzyl 2,2,2-trichloroethyl ether
3-Phenoxy-4-fluorobenzyl neopentyl ether
3-Phenoxy-4-fluorobenzyl 2,2,2-trichloroethyl ether
3-Phenoxy-4-fluorobenzyl 2-chloro-2-methylpropyl ether
3-(4-Chlorophenoxy)-4-fluorobenzyl neopentyl ether
3-(4-Bromophenoxy)-4-fluorobenzyl neopentyl ether
3-(2,3,4,5,6-Pentafluorophenoxy)-4-fluorobenzyl neopentyl ether
3-(2,3,4,5,6-Pentafluoroanilino)-4-fluorobenzyl neopentyl ether Examples of the present compound produced by the above methods will be shown in Table 1, but the present compound is not limited to these examples only.

TABLE 1

| Compound No. | Structural formula | Refractive Index (°C.) |
| --- | --- | --- |
| (1) | 3-phenoxypyridine with CH$_2$—O—CH$_2$—C(CH$_3$)$_3$ | 1.5284 (23.0) |
| (2) | 2-fluoro-N-phenylaniline with CH$_2$—O—CH$_2$—C(CH$_3$)$_3$ | 1.5522 (25.5) |
| (3) | 4-fluoro-3-phenoxybenzyl with CH$_2$—O—CH$_2$—C(CH$_3$)$_3$ | 1.5197 (21.0) |
| (4) | 3-phenoxypyridine with CH$_2$—O—CH$_2$—CCl$_3$ | 1.5670 (24.0) |
| (5) | 2-fluoro-N-phenylaniline with CH$_2$—O—CH$_2$—CCl$_3$ | 1.5965 (21.5) |

TABLE 1-continued
| Compound No. | Structural formula | Refractive Index (°C.) |
|---|---|---|
| (6) | 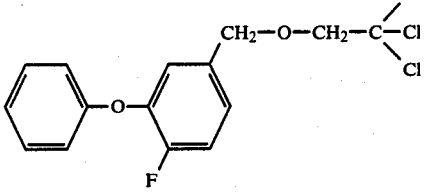 | 1.5591 (24.5) |
| (7) | 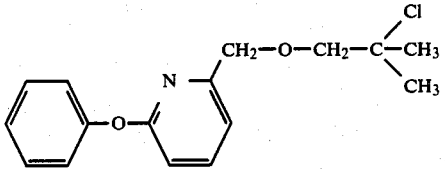 | 1.5461 (20.0) |
| (8) | 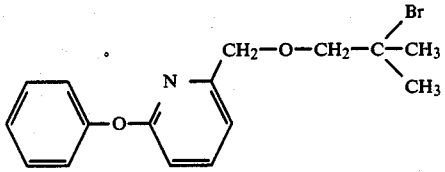 | 1.5835 (20.0) |
| (9) | 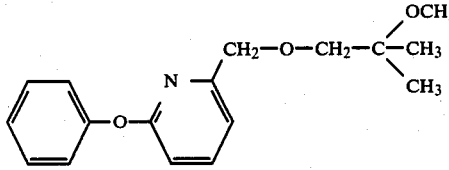 | 1.5328 (26.5) |
| (10) | 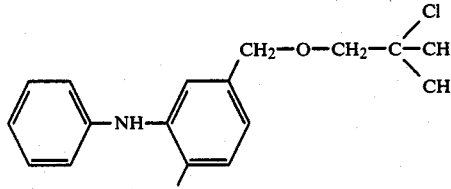 | 1.5531 (22.5) |
| (11) | 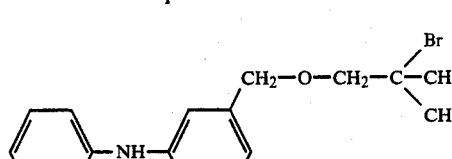 | 1.5718 (24.0) |
| (12) | 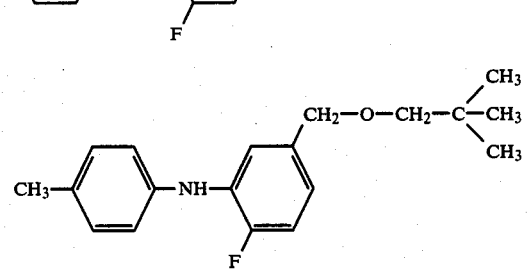 | 1.5496 (21.0) |
| (13) | 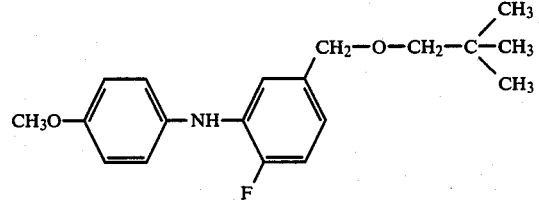 | 1.5550 (19.0) |

TABLE 1-continued

| Compound No. | Structural formula | Refractive Index (°C.) |
|---|---|---|
| (14) | 4-Cl-C6H4-NH-(2-F,5-(CH2-O-CH2-C(CH3)3)-C6H3) | 1.5643 (21.5) |
| (15) | 4-Br-C6H4-NH-(2-F,5-(CH2-O-CH2-C(CH3)3)-C6H3) | 1.5806 (19.5) |
| (16) | 4-Br-C6H4-O-(2-F,5-(CH2-O-CH2-C(CH3)3)-C6H3) | 1.5394 (18.0) |
| (17) | C6H5-O-(2-F,5-(CH2-O-CH2-C(Cl)(CH3)2)-C6H3) | 1.5334 (23.5) |
| (18) | 4-F-C6H4-O-(2-F,5-(CH2-O-CH2-C(CH3)3)-C6H3) | 1.5047 (24.0) |
| (19) | 4-Cl-C6H4-O-(2-F,5-(CH2-O-CH2-C(CH3)3)-C6H3) | 1.5188 (25.0) |
| (20) | 4-CH3-C6H4-O-(2-F,5-(CH2-O-CH2-C(CH3)3)-C6H3) | 1.5206 (21.5) |

TABLE 1-continued
| Compound No. | Structural formula | Refractive Index (°C.) |
|---|---|---|
| (21) | 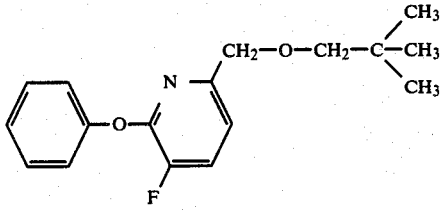 | 1.5184 (25.0) |
| (22) | 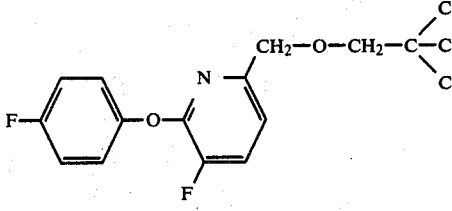 | 1.5039 (26.0) |
| (23) | 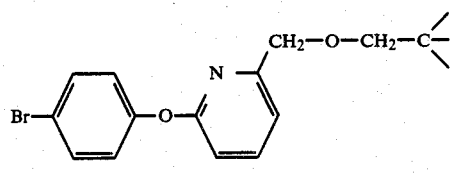 | 1.5476 (19.5) |
| (24) | 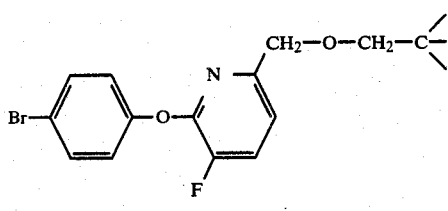 | 1.5388 (20.0) |
| (25) | 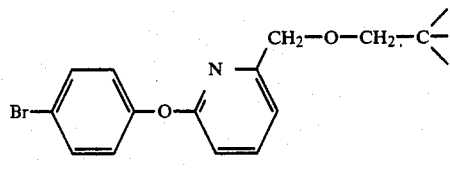 | 1.5872 (23.0) |
| (26) | 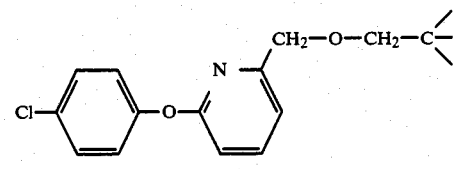 | 1.5358 (21.0) |
| (27) | 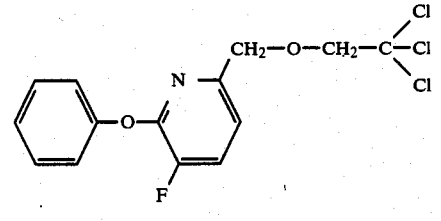 | 1.5546 (23.5) |
| (28) | 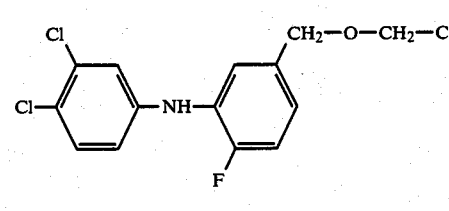 | 1.5730 (19.0) |

TABLE 1-continued

| Compound No. | Structural formula | Refractive Index (°C.) |
|---|---|---|
| (29) | 4-Cl-2-F-C6H3-NH-C6H3(2-F)(5-CH2-O-CH2-C(CH3)3) | 1.5394 (23.0) |
| (30) | 2-F-C6H4-NH-C6H3(2-F)(5-CH2-O-CH2-C(CH3)3) | 1.5189 (24.0) |
| (31) | 2,6-F2-C6H3-NH-C6H3(2-F)(5-CH2-O-CH2-C(CH3)3) | 1.5120 (26.0) |
| (32) | 4-CF3-C6H4-NH-C6H3(2-F)(5-CH2-O-CH2-C(CH3)3) | 1.5174 (20.0) |
| (33) | 4-CHF2O-C6H4-O-C6H3(2-F)(5-CH2-O-CH2-C(CH3)3) | 1.5004 (20.5) |
| (34) | C6H5-O-C6H3(2-F)(5-CH2-O-CH2-C(CH3)2(OCH3)) | 1.5239 (22.0) |
| (35) | 4-CH3-C6H4-O-(pyridine-2,6-diyl)-CH2-O-CH2-C(CH3)3 | 1.5311 (23.0) |

EXAMPLE 1

Synthesis of Compound (4) by the Method A 1.0 Gram of 2-chloromethyl-6-phenoxypyridine and 1.69 g of 2,2,2-trichloroethanol were added to 30 ml of dry acetone, and after adding 1.57 g of potassium carbonate thereto, the mixture was heated to reflux for 36 hours under a nitrogen atmosphere. The reaction mixture was cooled to room temperature, poured into ice water and extracted twice with diethyl ether. The ether layers were combined, washed with water and saturated sodium chloride solution and dried over anhydrous magnesium sulfate. The solvent was removed under a reduced pressure, and the residue was subjected to column chromatography on silica gel [eluted with n-hexane/ethyl acetate (50:1) mixture] to obtain 260 mg of the desired compound.

$n_D^{24.0}$ 1.5670;

NMR spectrum (in deuterio chloroform with TMS as an internal standard): δ (ppm) 4.20 (s, 2H), 4.81 (s, 2H), 6.80–7.82 (m, 8H).

EXAMPLE 2

Synthesis of Compound (7) by the Method B 0.78 Gram of 2-methallyloxymethyl-6-phenoxypyridine was dissolved in 20 ml of acetic acid, and hydrogen chloride gas was introduced into the solution for 30 minutes with ice-cooling.

Thereafter, 50 ml of toluene was added to the reaction mixture which was then neutralized with 5% aqueous sodium hydroxide solution with ice-cooling, and the toluene layer was separated and dried over anhydrous magnesium sulfate. The solvent was removed under a reduced pressure, and the residue was subjected to column chromatography on silica gel [eluted with n-hexane/ethyl acetate (30:1) mixture] to obtain 310 mg of the desired compound.

$n_D^{20.0}$ 1.5461;

NMR spectrum (in deuterio chloroform with TMS as an internal standard): δ (ppm) 1.60 (s, 6H), 3.59 (s, 2H), 4.60 (s, 2H), 6.60–7.80 (m, 8H).

EXAMPLE 3

Synthesis of Compound (1) by the Method A

Under a nitrogen atmosphere, 381 mg of sodium hydride (63% oil dispersion) was added to 50 ml of dry DMF. A solution of 0.88 g of 2,2-dimethylpropanol in 5 ml of dry DMF was then added, and the reaction solution was heated to 50°–60° C. for 30 minutes. Thereafter, a solution of 2.04 g of 2-chloromethyl-6-phenoxypyridine in 5 ml of dry DMF was added at room temperature to the reaction solution, and the reaction mixture was kept at 50°–60° C. for 1 hour, followed by stirring over night at room temperature. The reaction mixture was poured into ice water and extracted twice with diethyl ether. The ether layers were combined, washed with saturated sodium chloride solution and dried over anhydrous magnesium sulfate. The solvent was removed under a reduced pressure, and the residue was subjected to column chromatography on silica gel [eluted with n-hexane/ethyl acetate (30:1) mixture] to obtain 2.18 g of the desired compound.

$n_D^{23.0}$ 1.5284;

NMR spectrum (in deuterio chloroform with TMS as an internal standard): δ (ppm) 0.98 (s, 9H), 3.20 (s, 2H), 4.51 (s, 2H), 6.5–7.7 (m, 8H).

EXAMPLE 4

Synthesis of Compound (2) by the Method C 1.5 Gram of 3-(N-acetylanilino)-4-fluorobenzyl neopentyl ether was dissolved in a mixture of 10 ml of methanol and 3 ml of water, and then 1.3 g of potassium hydroxide was added. The reaction solution was heated to 60°–65° C. and stirred at this temperature for 12 hours. After cooling the reaction solution to room temperature, water and ether were added, and the aqueous layer was separated from the ether layer and extracted with ether. The ether layers were combined, washed with saturated sodium chloride solution and dried over anhydrous magnesium sulfate. The solvent was removed under a reduced pressure, and the residue was subjected to column chromatography on silica gel [eluted with n-hyxane/ethyl acetate (30:1) mixture] to obtain 0.96 g of the desired compound as an oily product.

$n_D^{25.5}$ 1.5522;

NMR spectrum (in deuterio chloroform with TMS as an internal standard): δ (ppm) 0.98 (s, 9H), 3.11 (s, 2H), 4.47 (s, 2H), 5.70–5.90 (b, 1H), 6.80–7.50 (m, 8H).

EXAMPLE 5

Synthesis of Compound (3) by the Method D

Under a nitrogen atmosphere, 0.32 g of sodium hydride (60% oil dispersion) was added to 20 ml of dry dimethylformamide, and 0.75 g of phenol was then added at room temperature. After evolution of hydrogen gas ceased, stirring was continued at 40°–50° C. for further 30 minutes. After cooling the reaction solution to room temperature, 2.2 g of 3-bromo-4-fluorobenzyl neopentyl ether and 500 mg of anhydrous cuprous chloride were added thereto, and the reaction mixture was heated at 140°–145° C. for 8 hours. After cooling the reaction mixture, water and ether were added, and the aqueous layer was separated from the ether layer and extracted with ether. The ether layers were combined, washed with 5% aqueous hydrochloric acid, 10% aqueous sodium hydroxide and saturated sodium chloride solution successively and dried over anhydrous magnesium sulfate. The solvent was removed under a reduced pressure, and the residue was subjected to column chromatography on silica gel [eluted with n-hexane/ethyl acetate (50:1) mixture] to obtain 1.12 g of the desired compound.

$n_D^{21.0}$ 1.5197;

NMR spectrum (in deuterio chloroform; with TMS as an internal standard): δ (ppm) 0.88 (s, 9H), 3.08 (s, 2H), 4.40 (s, 2H), 6.70–7.50 (m, 8H).

EXAMPLE 6

Synthesis of Compound (35) by the Method D

Under a nitrogen atmosphere, 0.22 g of sodium hydride (60% oil dispersion) was added to 20 ml of dry dimethylformamide, and 0.61 g of p-cresol was then added thereto. The reaction solution was heated to 50°–60° C. and kept at this temperature for 30 minutes. After cooling the reaction solution to room temperature, 1.2 g of 6-chloro-2-pyridylmethyl neopentyl ether and then 200 mg of anhydrous cuprous chloride were added to the reaction solution. The reaction mixture was heated to 130°–140° C. and kept at this temperature for 5 hours. Subsequently, the same work up procedures as in Example 5 were carried out to obtain 0.41 g of the desired compound.

$n_D^{23.0}$ 1.5311;

NMR spectrum (in deuterio chloroform with TMS as an internal standard): δ (ppm) 0.95 (s, 9H), 2.36 (s, 3H), 3.15 (s, 2H), 4.45 (s, 2H), 6.80–7.80 (m, 7H).

EXAMPLE 7

Synthesis of Compound (14) by the Method C 0.6 Gram of 3-(N-acetyl-4-chloroanilino)-4-fluorobenzyl neopentyl ether was dissolved in 10 ml of methanol, and then 300 mg of potassium hydroxide and 2 ml of water were added to the resulting solution. The reaction mixture was stirred for 5 hours at 60° C. Subsequently, the same work up procedures as in Example 4 were employed to obtain 0.43 g of the desired compound.

$n_D^{21.5}$ 1.5643;

NMR spectrum (in deuterio chloroform with TMS as an internal standard): δ (ppm) 0.91 (s, 9H), 3.10 (s, 2H), 4.42 (s, 2H), 5.70–5.90 (b, 1H), 6.80–7.45 (m, 7H)

EXAMPLE 8

Synthesis of compound (34) by the Method B 0.65 Gram of 3-phenoxy-4-fluorobenzyl methallyl ether was dissolved in 15 ml of methanol, and 0.84 g of mercuric acetate was added thereto at room temperature. The reaction mixture was stirred at room temperature over night, the reaction mixture was then cooled to 0°–5° C., and 0.37 g of potassium hydroxide and 0.25 g of sodium borohydride were added thereto. The reaction solution was filtrated through a celite pad, and water was added to the filtrate, followed by extraction with ether. The ether layer was washed with saturated sodium chloride solution and dried over anhydrous magnesium sulfate. The solvent was removed under a reduced pressure, and the residue was subjected to column chromatography on silica gel [eluted with n-hexane/ethyl acetate (10:1) mixture] to obtain 320 mg of the desired compound.

$n_D^{22.0}$ 1.5239;

NMR spectrum (in deuterio chloroform with TMS as an internal standard): δ (ppm) 1.20 (s, 6H), 3.21 (s, 3H), 3.40 (s, 2H), 4.41 (s, 2H), 6.71–7.52 (m, 8H).

EXAMPLE 9

Synthesis of Compound (23) by Method A

Under a nitrogen atmosphere, 160 mg of sodium hydride (60% oil dispersion) was added to 20 ml of dry dimethylformamide, and 360 mg of neopentyl alcohol was then added thereto. The mixture was heated to 50°–60° C. for 30 minutes. After evolution of hydrogen gas ceased, the reaction mixture was cooled with ice bath, and 1.0 g of 6-(4-bromophenoxy)-2-chloromethylpyridine was added thereto. The reaction mixture was then stirred at room temperature for 1 hour and at 50° C. for 3 hours. The resulting solution was poured into ice water, and subsequently worked up the same procedures as in Example 3 to obtain 0.42 g of the desired compound.

$n_D^{19.5}$ 1.5476;

NMR spectrum (in deuterio chloroform with TMS as an internal standard): δ (ppm) 0.97 (s, 9H), 3.17 (s, 2H), 4.48 (s, 2H), 6.72–7.89 (m, 7H).

When the present compounds are used as an active ingredient for an insecticidal and acaricidal composition, they may be used as it is without adding any other ingredients. Generally, however, they are formulated into emulsifiable concentrates, wettable powders, dusts, granules, oil sprays, aerosols, heating fumigants (e.g. mosquito coils, electric mosquito mats), foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carrier, mat, etc.

These preparations contain 0.01 to 95% by weight of the present compound as an active ingredient.

The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydofuran, esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl) sulfonates, diakyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as sticking agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oil, the foregoing surface active agents, antioxidants (e.g. BHT, BHA), fatty acid salts (e.g. sodium oleate, calcium stearate), fatty acid esters (e.g. methyl oleate, methyl stearate) and the like.

Next, formulation examples will be shown. The present compounds are shown by Compound No. described in Table 1. Parts in the examples are by weight.

Formulation example 1

0.2 Part of each of the present compounds (2), (3) and (4), 2 parts of xylene and 97.8 parts of kerosene are mixed to obtain the oil spray of each compound.

Formulation example 2

10 Parts of each of the present compounds (1) to (35), 14 parts of polyoxyethylene styrylphenyl ether, 6 parts of calcium dodecylbenzenesulfonate and 70 parts of xylene are well mixed to obtain the emulsifiable concentrate of each compound.

Formulation example 3

20 Parts of each of the present compounds (2), (3) and (7), 10 parts of fenitrothion, 3 parts of calcium lignosulfonate, 2 parts of sodium lauryl sulfate and 65 parts of synthetic hydrated silicon dioxide are well pulverized and mixed together to obtain the wettable powder of each compound.

Formulation example 4

One part of each of the present compounds (2), (3) and (8), 2 parts of Carbaryl, 87 parts of kaolin clay and 10 parts of talc are well pulverized and mixed together to obtain the dust of each compound.

Formulation example 5

5 Parts of each of the present compounds (2), (3) and (34), 1 part of synthetic hydrated silicon dioxide, 2 parts of calcium lignosulfonate, 30 parts of bentonite and 62 parts of kaolin clay are well pulverized and mixed thoroughly, kneaded well with water, granulated and then dried to obtain the granules of each compound.

Formulation example 6

0.05 Part of each of the present compounds (1), (2) and (3), 0.2 part of tetramethrin, 0.05 part of resmethrin, 7 parts of xylene and 32.7 parts of deodorized kerosene are well mixed into a solution. The solution is filled in an aerosol container, and after attaching a valve portion to the container, 60 parts of propellant (liquefied petroleum gas) is charged therein through the valve under pressure to obtain the aerosol of each compound.

Formulation example 7

0.3 Gram of each of the present compounds (1), (2) and (3) and 0.3 g of the d-trans chrysanthemate of allethrin are dissolved in 20 ml of methanol. This solution and 99.4 g of a mosquito coil carrier, which is a 3:5:1 mixture of Tabu powder, Pyrethrum marc and wood powder, are uniformly mixed with stirring. After evaporating methanol, 150 ml of water is added to the residue, and the mixture is well kneaded, shape and dried to obtain the mosquito coil of each compound.

These preparations are used as it is or as diluted solutons with water. Also, they may be used in mixture with other insecticides, acaricides, nematocides, fungicides, herbicides, plant growth regulators, fertlizers, soil improvers and the like.

When the present compound is used as an insecticidal and acaricidal composition, its dosage rate is generally 5 to 100 g per 10 areas. When emulsifiable concentrates, wettable powders, etc. are used as aqueous dilute solutions, the application concentration of the compound is 10 to 100 ppm. Dusts, granules, oil sprays, aerosols, etc. are used as it is without dilution.

Next, test examples will be shown. The present compounds are shown by Compound No. in Table 1, and compounds used as a control are shown by Compound symbol in Table 2.

TABLE 2

| Compound symbol | Structural formula | Name |
|---|---|---|
| (A) | 2-isopropylphenyl-N-methylcarbamate structure | BPMC |
| (B) | $(CH_3O)_2P(=S)SCH(COOC_2H_5)CH_2COOC_2H_5$ | Malathion |
| (C) | phenoxybenzyl ether structure | Compound described in U.K. Patent No. 1,570,982 |
| (D) | phenoxybenzyl-O-CH_2-CCl_3 structure | |
| (E) | $Cl\text{-}C_6H_3(CH_3)\text{-}N=CH\text{-}N(CH_3)_2$ | Chlordimeform |

Test example 1

The emulsifiable concentrates of the following present compounds and controls obtained according to Formulation example 2 were each diluted with water to a prescribed concentration, and the culm of rice plant (about 12 cm in length) was dipped for 1 minute in the resulting aqueous dilute solutions. After air-drying, the culm was placed in test tube, and 10 adults of a resistant strain of green rice leafhopper (Nephotettix cincticeps) were liberated in the tube. After one day, the dead and alive of the adult were examined to obtain $LC_{50}$ (50% lethal concentration) (two replications).

The result is shown in Table 3.

TABLE 3

| Test compound | $LC_{50}$ (ppm) | Test compound | $LC_{50}$ (ppm) |
|---|---|---|---|
| (1) | 5.4 | (19) | 43 |
| (2) | 1.5 | (20) | 8.7 |
| (3) | 1.3 | (21) | 4.5 |
| (4) | 11 | (22) | 1.3 |
| (5) | 66 | (23) | 7.4 |
| (6) | 21 | (24) | 6.2 |
| (7) | 15 | (26) | 1.5 |
| (8) | 32 | (27) | 9.2 |
| (9) | 99 | (29) | 3.5 |
| (10) | 45 | (32) | 12 |
| (11) | 94 | (34) | 6.8 |
| (12) | 10 | (35) | 17 |
| (14) | 50 | | |
| (16) | 13 | (A) | 190 |
| (17) | 2.4 | (B) | =500 |
| (18) | 2.0 | | |

Test example 2

The emulsifiable concentrates of the following present compounds and control obtained according to Formulaton example 2 were each diluted with water to a prescribed concentration, and the culm of rice plant (about 12 cm in length) was dipped for 1 minute in the resulting aqueous dilute solutions. After air-drying, the culm was placed in a test tube, and 10 adults of smaller brown planthopper (*Laodelphax striatellus*) were liberated in the tube. After one day, the dead and alive of the adult were examined to obtain $LC_{50}$ (50% lethal concentration) (two replications).

The result is shown in Table 4

TABLE 4

| Test compound | $LC_{50}$ (ppm) |
|---|---|
| (1) | 15 |
| (3) | 33 |
| (4) | 15 |
| (7) | 90 |
| (17) | 18 |
| (18) | 50 |
| (C) | 130 |

Test example 3

The emulsifiable concentrates of the following present compounds and controls obtained according to Formulation example 2 were each diluted with water to a prescribed concentration, and the culm of rice plant (about 12 cm in length) was dipped for 1 minute in the resulting aqueous dilute solutions. After air-drying, the culm was placed in a test tube, and 10 adults of brown rice planthopper (*Nilaparvata lugens*) were liberated in the tube. After one day, the dead and alive of the adult were examined to obtain $LC_{50}$ (50% lethal concentration) (two replications).

The result is shown in Table 5.

TABLE 5

| Test compound | $LC_{50}$ (ppm) | Test compound | $LC_{50}$ (ppm) |
|---|---|---|---|
| (1) | 3.4 | (17) | 22 |
| (2) | 1.5 | (18) | 39 |
| (3) | 26 | (19) | 7.6 |
| (4) | 6.7 | (20) | 6.9 |
| (5) | 50 | (23) | 17 |
| (6) | 30 | (26) | 19 |
| (7) | 39 | (29) | 38 |
| (10) | 18 | (32) | 15 |
| (11) | 50 | (34) | 40 |
| (12) | 13 | (35) | 29 |
| (14) | 11 | | |
| (15) | 52 | (C) | 150 |
| (16) | 36 | (D) | 170 |

Test example 4

On the bottom of a polyethylene cup of 5.5 cm in diameter was placed a piece of filter paper of the same size as the bottom, and 0.7 ml of a test solution, prepared by diluting the emulsifiable concentrates of the following present compounds and control prepared according to Formulation example 2 to a prescribed concentration with water, was added dropwise to the filter paper. Thirty milligrams of sucrose were uniformly placed in the filter paper as bait. Thereafter, 10 housefly female adults (*Musca domestica*) were liberated in the cup which was then covered with a lid. After 48 hours, the dead and alive were examined to obtain $LC_{50}$ (50% lethal concentration) (two replications).

The result is shown in Table 6.

TABLE 6

| Test compound | $LC_{50}$ (ppm) | Test compound | $LC_{50}$ (ppm) |
|---|---|---|---|
| (1) | 37 | (16) | 53 |
| (2) | 150 | (17) | 97 |

TABLE 6-continued

| Test compound | $LC_{50}$ (ppm) | Test compound | $LC_{50}$ (ppm) |
|---|---|---|---|
| (3) | 22 | (18) | 33 |
| (4) | 210 | (19) | 44 |
| (6) | 78 | (23) | 28 |
| (7) | 92 | (25) | 98 |
| (8) | 140 | (28) | 29 |
| (10) | 230 | (29) | 150 |
| (13) | 250 | (35) | 99 |
| (14) | 150 | | |
| (15) | 180 | (D) | 400 |

Test example 5

The following present compounds and controls were diluted with acetone, and the dilute solutions were each uniformly coated onto the bottom (bottom area, 78.5 cm$^2$) of an aluminum dish (inside diameter, 10 cm; height, 3 cm) so that the amount of the active ingredient was 73 mg/m$^2$. After air-drying, 10 German cockroach adults (5 males and 5 females) (*Blattella germanica*) were liberated in the dish and forced to contact with the treated bottom of the dish. After forced contact for 24 hours, the test insects were transferred to a new vessel and bred with water and bait. After 72 hours, the dead and alive were examined to obtain mortality (two replications).

The result is shown in Table 7.

TABLE 7

| Test compound | Mortality (%) | Test compound | Mortality (%) |
|---|---|---|---|
| (1) | 100 | (15) | 100 |
| (2) | 100 | (21) | 100 |
| (3) | 80 | (22) | 100 |
| (5) | 100 | (25) | 90 |
| (6) | 90 | (26) | 100 |
| (7) | 100 | (27) | 100 |
| (8) | 100 | (32) | 100 |
| (10) | 100 | (35) | 100 |
| (11) | 100 | | |
| (12) | 100 | (C) | 0 |
| (14) | 100 | (D) | 20 |
| | | No treatment | 0 |

Test example 6

Two milliliters each of the 200-fold aqueous dilute solutions (corresponding to 500 ppm), prepared from the emulsifiable concentrates of the following present compounds and controls obtained according to Formulation example 2, were infiltrated into 13 g of artificial feed for common cutworm (*Spodoptera litura*). The feed was then placed in a polyethylene cup of 11 cm in diameter, and 10 fourth instar larvae of common cutworm were liberated therein. After six days, the dead and alive were examined (two replications).

The result is shown in Table 8.

TABLE 8

| Test compound | Mortality (%) | Test compound | Mortality (%) |
|---|---|---|---|
| (1) | 95 | (21) | 100 |
| (2) | 100 | (22) | 100 |
| (3) | 100 | (23) | 100 |
| (5) | 100 | (24) | 100 |
| (6) | 100 | (25) | 95 |
| (7) | 85 | (26) | 100 |
| (10) | 100 | (27) | 100 |
| (11) | 100 | (28) | 100 |

TABLE 8-continued

| Test compound | Mortality (%) | Test compound | Mortality (%) |
| --- | --- | --- | --- |
| (12) | 100 | (29) | 100 |
| (13) | 100 | (30) | 100 |
| (14) | 100 | (31) | 100 |
| (15) | 100 | (32) | 100 |
| (16) | 100 | (33) | 100 |
| (17) | 100 | (35) | 100 |
| (18) | 100 | | |
| (19) | 100 | (C) | 15 |
| (20) | 100 | (D) | 10 |
| | | No treatment | 5 |

Test example 7

The female adults of carmine spider mite (*Tetranychus cinnabarinus*) were put at a rate of 10 adults/leaf on the leaves of potted kidney bean (at the primary leaf stage) which had elapsed 7 days after sowing, and placed in a constant-temperature room kept at 25° C. After 6 days, the 200-fold aqueous dilute solutions (corresponding to 500 ppm), prepared from the emulsifiable concentrates of the following present compounds and controls prepared according to Formulation example 2, were each sprayed at a rate of 15 ml/pot by means of a turn table. At the same time, the soil in the pot was injected with 2 ml of each aqueous dilute solution. After 8 days, the degree of damage of the plant by the mite was examined.

Standard for the judgement of the effect:
—: Little damage is observed.
+: Slight damage is observed.
++: The same damage as in the untreated plot is observed.

The result is shown in Table 9.

TABLE 9

| Test compound | Degree of damage | Test compound | Degree of damage |
| --- | --- | --- | --- |
| (5) | — to + | (C) | ++ |
| (6) | — | (D) | ++ |
| (10) | — to + | (E) | — to + |
| (11) | — to + | | |
| (14) | — | No treatment | ++ |
| (15) | — | | |

What is claimed is:

1. An ether compound represented by the general formula

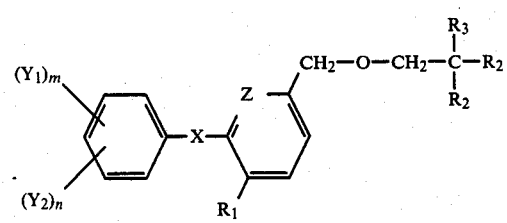

wherein X represents an oxygen atom or a group represented by the formula —NH—; Z represents —CH= or a nitrogen atom; $R_1$ represents fluorine or a hydrogen atom; $Y_1$ and $Y_2$, which may be identical or different, represent a hydrogen or halogen atom or an alkyl, haloalkyl, akoxyl or haloalkoxy group; m and n represent an integer of 1 to 4 and the sum of them is not more than 5; $R_2$ represents a methyl group or a chlorine atom; and $R_3$ represents a methyl group, a halogen atom or a methoxy group; with the proviso that (i) when X is oxygen and Z is CH, $R_1$ is fluorine; (ii) when X is NH, Z is CH.

2. The ether compound according to claim 1, wherein one of $Y_1$ and $Y_2$ represents hydrogen atom and the other represents a hydrogen or halogen atom or an alkyl group; the sum of m and n is 2; and $R_3$ represents a methyl group or a halogen atom.

3. The ether compound according to claim 1, wherein X represents a group represented by the formula —NH—, or X represents an oxygen atom and Z represents a nitrogen atom; one of $Y_1$ and $Y_2$ represents a hydrogen atom and the other represents a hydrogen, chlorine or bromine atom or a methyl group; the sum of m and n is 2; and both $R_2$ and $R_3$ are identical each other and represent a methyl group or a chlorine atom.

4. A compound of the formula,

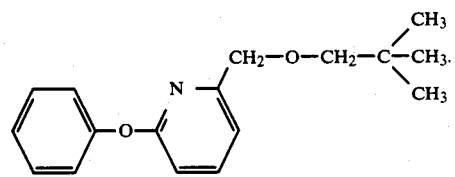

5. A compound of the formula,

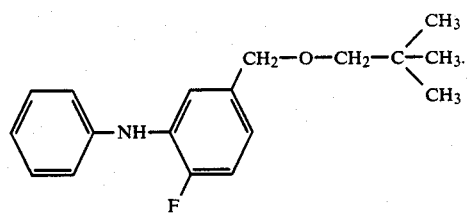

6. A compound of the formula,

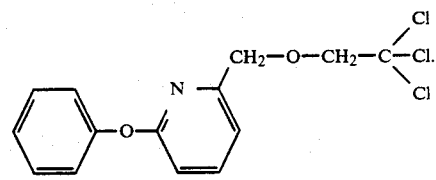

7. A compound of the formula,

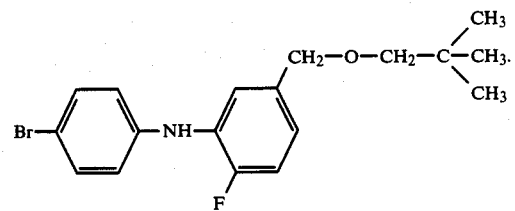

8. A compound of the formula,

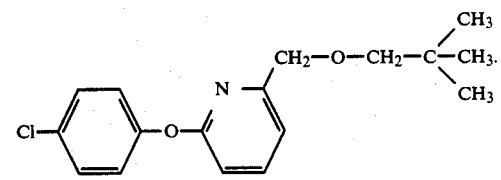

9. A compound of the formula,

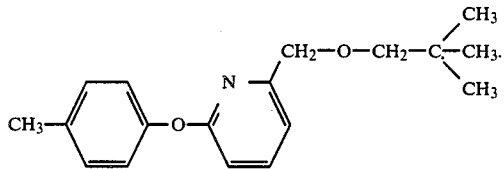

10. A compound of the formula,

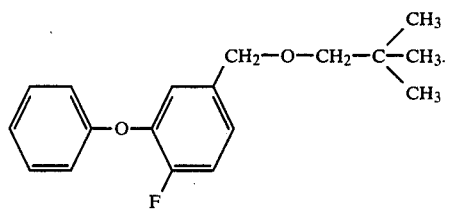

11. An insecticidal an acaricidal composition which comprises as an active ingredient an insecticidally or acaricidally effective amount of the ether compound according to claim 1 or an inert carrier.

12. A method for controlling an insect or an acarid which comprises applying an insecticidally or acaricidally effective amount of the ether compound according to claim 1 to the insect or the acarid.

13. A method for controlling an insect or an acarid which comprises applying an insectidially or acaricidally effective amount of the ether compound according to claim 2 to the insect or the acarid.

14. A method for controlling an insect or an acarid which comprises applying an insecticidally or acaricidally effective amount of the ether compound according to claim 3 to the insect or the acarid.

15. An insecticidal and acaricidal composition which comprises as an active ingredient an insecticidally and acaricidally effective amount of the ether comound according to claim 2 and an inert carrier.

16. An insecticidal and acaricidal composition which comprises as an active ingredient an insecticidally and acaricidally effective amount of the ether compound according to claim 3 and an inert carrier.

* * * * *